United States Patent [19]

Marsden

[11] 4,143,129
[45] Mar. 6, 1979

[54] CEPHALEXIN TABLETS

[75] Inventor: Richard Marsden, Bisley, England

[73] Assignee: Lilly Industries Limited, London, England

[21] Appl. No.: 869,982

[22] Filed: Jan. 16, 1978

Related U.S. Application Data

[63] Continuation of Ser. No. 731,193, Oct. 12, 1976, abandoned.

[30] Foreign Application Priority Data

Oct. 11, 1975 [GB] United Kingdom ............... 41744/75

[51] Int. Cl.$^2$ .................... A61K 47/00; A61K 31/79; A61K 9/20
[52] U.S. Cl. ...................................... 424/80; 424/246
[58] Field of Search ................................. 424/80, 246

[56] References Cited

U.S. PATENT DOCUMENTS

| | | | |
|---|---|---|---|
| 3,034,911 | 5/1962 | McKee et al. | 424/361 X |
| 3,424,842 | 1/1969 | Nurnberg | 424/94 |
| 3,622,677 | 11/1971 | Short et al. | 424/361 X |
| 3,632,778 | 1/1972 | Sheth et al. | 424/319 |
| 3,931,404 | 1/1976 | Fulberth et al. | 424/246 |

FOREIGN PATENT DOCUMENTS 2355204 5/1974 Fed. Rep. of Germany.
2259646 6/1974 Fed. Rep. of Germany.
2424950 12/1974 Fed. Rep. of Germany.

Primary Examiner—Shep K. Rose
Attorney, Agent, or Firm—Steven R. Lammert; Everet F. Smith

[57] ABSTRACT

A small tablet containing over 90% by weight of an orally active cephalosporin such as cephalexin and which utilizes as a binder polyvinyl pyrrolidone having a number average molecular weight of from 500,000 to 1,500,000.

4 Claims, No Drawings

CEPHALEXIN TABLETS

This is a continuation, of application Ser. No. 731,193 filed Oct. 12, 1976, now abandoned.

This invention relates to pharmaceutical formulations, more particularly to tablets containing an orally active cephalosporin such as cephalexin or cephradine.

Both cephalexin (7-(D-α-amino-phenylacetamido)-3-methyl-3-cephem-4-carboxylic acid) and cephradine (7-[D-α-amino-(1,4-cyclohexadienyl)-acetamido]-3-methyl-3-cephem-4-carboxylic acid) are excellent broad spectrum antibiotics having low toxicity. However, for effective chemotherapy of bacterial infections in humans it has been found that quite high dosages are needed. Consequentially, heretofore, administration of these cephalosporins has necessarily taken the form of either rather large tablets or numerous small tablets. Both of these forms of administration have undesirable facets so far as patient acceptability, particularly in children and the elderly, is concerned. Thus, there has long been a need for smaller tablets containing adequate amounts of active ingredient.

Accordingly, the present invention provides a tablet which comprises:
(a) greater than 90% by weight of an orally active cephalosporin;
(b) less than 10% by weight of excipients which comprise:
  (i) from 2 to 5% by weight of a binder which is polyvinyl pyrrolidone having a number average molecular weight of from 500,000 to 1,500,000;
  (ii) from 1.5 to 5% by weight of a disintegrant; and
  (iii) from 0.3 to 2% by weight of a lubricant, and which has
(c) a diametral crushing strength of from 5.0 to 15.0 Kg.; and
(d) will disintegrate in distilled water within 15 minutes at 37° C.

Preferably, the excipients will comprise from 2 to 4% by weight of binder, from 1.5 to 4% by weight of disintegrant and from 0.3 to 2% by weight of lubricant.

The tablet will contain approximately from 90 to 96%, preferably from 92 to 95% most preferably from 93 to 95%, by weight of the orally active cephalosporin. The preferred cephalosporin is cephalexin, which is particularly useful in the practice of the invention when it is in the form of its monohydrate.

The use of polyvinyl pyrrolidone having a number average molecular weight of from 500,000 to 1,000,000 ideally approximately 700,000, as determined by viscosity measurements, as the binder is much preferred.

The disintegrant is preferably a sodium starch glycolate containing from 15 to 35, most preferabiy about 25, carboxymethyl groups per 100 glucose units, although other disintegrants such as zeolites of the type known by the trade name "Amberlite IRP 88", or sodium carboxymethylcellulose may be used.

Similarly, although the use of magnesium stearate as the lubricant is preferred, other lubricants such as stearic acid or calcium stearate can also be used.

Physicians commonly administer orally active cephalosporins in the form of tablets containing approximately 250, 500 or 1000 mg. of the active ingredient. Accordingly, in three further aspects of the invention there are provided:

(A) a tablet which contains approximately 250 mg. of an orally active cephalosporin, and which has a volume of from 0.20 to 0.23 ml., when determined by displacement of liquid paraffin;

(B) a tablet which contains approximately 500 mg. of an orally active cephalosporin, and which has a volume of from 0.40-0.47 ml., when determined by displacement of liquid paraffin; and (C) a tablet which contains approximately 1000 mg. of an orally active cephalosporin, and which has a volume of from 0.80 to 0.95 ml., when determined by displacement of liquid paraffin.

The tablets of the invention may also comprise small amounts of other commonly used excipients, for instance they may be coloured by the use of suitable dyes or lakes.

In addition, if desired, the tablets of the invention may be coated using a polymer coating agent which is, for example, a cellulose derivative such as hydroxypropyl cellulose, hydroxypropylmethyl cellulose or methyl cellulose.

The tablets of the invention can be prepared by dissolving or dispersing the binder in water or a suitable organic solvent and using this solution or dispersion to mass and subsequently granulate the cephalosporin. The granules are then passed through a sieve of suitable mesh size and dried. After resieving to break up any agglomerates the dried granules are combined with the lubricant and disintegrant and compressed into tablets using a conventional tabletting machine. If it is desired to produce coloured tablets, a dye may be added to the solution or dispersion of binder, or a lake to the dried powder blend prior to compression. Coating of the tablets may be carried out subsequent to compression using appropriate coating equipment.

To further illustrate the invention and to show how the same may be carried into effect, reference will now be made to the following nonlimitative examples.

EXAMPLE 1

This is an example of a conventional tablet containing cephalexin. The ingredients were:

| | | mg. |
|---|---|---|
| Cephalexin monohydrate* | | 1000 |
| 'Primojel'+ | | 44.4 |
| Pregelatinised Starch | | 70 |
| Flowable Starch | | 55.7 |
| Magnesium Stearate | | 14.8 |
| Stearic Acid | | 29.6 |
| Starch dried | q.s. | 1480 |

*as determined by iodometric assay
+trademark
'Primojel' is the trade name for a sodium starch glycolate containing approximately 25 carboxymethyl units per 100 glucose units.

The above ingredients were formulated into a tablet using conventional procedure.

Although the tablet prepared from the above ingredients was satisfactory, its volume was 1.15 ml. (as measured by displacement of liquid paraffin).

EXAMPLE 2

This is an example of a tablet of the invention.

| | mg. |
|---|---|
| Cephalexin monohydrate* | 1000 |
| 'Kollidon 90'+ | 24 |
| 'Primojel'+ | 20 |
| Magnesium Stearate | 6 |
| Total | 1050 |

*as determined by iodometric assay
+trademark

The 'Kollidon 90', which is a polyvinyl pyrrolidone having a number average molecular weight of approximately 700,000, as determined by viscosity measurements, was dissolved in water and then massed with the cephalexin monohydrate so as to form a granular material. After sieving, this material was dried and then resieved. The resieved mixture was then combined and intimately admixed with the 'Primojel' and magnesium stearate and compressed into a tablet.

The volume of the tablet, when measured by displacement of liquid paraffin, was 0.87 ml. It will be immediately appreciated that this is significantly less than the volume of the conventional tablet of Example 1.

The diametral crushing strength of this tablet, which is of course a measure of the hardness of the tablet, was measured using an Erweka tester type TBT (Erweka Apparatebau GmbH., Frankfurt am Main, W. Germany) and was found to be 12 Kg., a quite satisfactory hardness. In addition, the disintegration time of this tablet was determined using the method described in the British Pharmacopoeia 1973 Appendix XIX A, pages A 131/2, i.e. in distilled water at 37° C. ± 2° C. and was found to be 4 minutes, a good disintegration time.

EXAMPLES 3 AND 4

Using the procedure of Example 2, there were prepared tablets containing the ingredients listed below.

|  | mg. |
|---|---|
| Cephalexin monohydrate* | 500 |
| 'Primojel'+ | 14 |
| 'Kollidon 90'+ | 15 |
| Magnesium Stearate | 6 |
| Total | 535 |

Volume 0.43 ml.
Diametral Crushing Strength 11 Kg.
Disintegration Time 5 minutes.

|  | mg. |
|---|---|
| Cephalexin monohydrate* | 250 |
| 'Primojel'+ | 8 |
| 'Kollidon 90'+ | 8 |
| Magnesium Stearate | 4 |
|  | 270 |

*as determined by iodometric assay
+trademark
Volume 0.23 ml.
Diametral Crushing Strength 10 Kg.
Disintegration Time 6 minutes.

Similarly, using the method described in Example 2, the following further tablets were prepared.

EXAMPLE 5

|  | mg. |
|---|---|
| Cephalexin monohydrate* | 1000 |
| 'Kollidon 90'+ | 20 |
| 'Primojel'+ | 15 |
| Magnesium Stearate uz,24/27 3 |  |
|  | 1038 |

*as determined by iodometric assay
+trademark
Volume 0.856 ml.
Diametral Crushing Strength 10.5 Kg.
Disintegration Time 3 minutes.

EXAMPLE 6

|  | mg. |
|---|---|
| Cephalexin monohydrate* | 1000 |
| 'Kollidon 90'+ | 20 |
| 'Amberlite IRP 88'+ | 15 |
| Magnesium Stearate | 3 |
|  | 1038 |

*as determined by iodometric assay
+trademark
Volume 0.849 ml.
Diametral Crushing Strength 14.2 Kg.
Disintegration Time 5 minutes.

EXAMPLE 7

|  | mg. |
|---|---|
| Cephalexin monohydrate* | 1000 |
| 'Kollidon 90'+ | 25 |
| 'Primojel'+ | 20 |
| Stearic Acid | 7 |
|  | 1052 |

*as determined by iodometric assay
+trademark
Volume 0.872 ml.
Diametral Crushing Strength 14 Kg.
Disintegration Time 13 minutes.

EXAMPLE 8

|  | mg. |
|---|---|
| Cephalexin monohydrate* | 1000 |
| 'Kollidon 90'+ | 20 |
| 'Primojel'+ | 15 |
| Stearic acid | 7 |
| F.D. & C. Yellow No. 6 Aluminium Lake | 10 |
|  | 1052 |

*as determined by iodometric assay
+trademark
Volume 0.910 ml.
Diametral Crushing Strength 10 Kg.
Disintegration Time 2 minutes The F.D. & C. Yellow No. 6 Aluminium Lake used in Example 8 was combined with the 'Primojel' and the stearic acid and then mixed with cephalexin granules formed as in Example 2. The mixture thus formed was then compressed into a tablet.

What is claimed is:

1. A pharmaceutical tablet comprised of:
   (a) from about 90% to about 96 percent by weight of orally active cephalexin;
   (b) from about 4 to about 10 percent by weight of excipients comprising:
      (i) from about 2 to about 5 percent by weight of polyvinyl pyrrolidone having an average molecular weight of from about 500,000 to about 1,500,000;
      (ii) from about 1.5 to about 5 percent by weight of a disintegrant selected from the group consisting of sodium starch glycolate, sodium carboxymethylcellulose, and a weakly acidic methacrylic acid-divinylbenzene copolymer zeolite; and (iii) from about 0.3 to about 2 percent by weight of a pharmaceutically acceptable lubricant, and having (c) a diametral crushing strength of from about 5.0 to about 15.0 Kg; and (d) a disintegration time in distilled water of 15 minutes or less at 37° C.

2. A tablet according to claim 1 wherein the orally active cephalexin is 7-(D-α-amino-phenylacetamido)-3-methyl-3-cephem-4-carboxylic acid, monohydrate.

3. A tablet according to claim 1 wherein the disintegrant is a sodium starch glycolate containing from 15 to 35, most preferably about 25, carboxymethyl groups per 100 glucose units.

4. A tablet according to claim 1 which contains approximately 1000 mg. of cephalexin and which has a volume of from about 0.80 to about 0.95 ml., when determined by displacement of liquid paraffin.

* * * * *